United States Patent [19]

Soma et al.

[11] Patent Number: 5,382,430

[45] Date of Patent: Jan. 17, 1995

[54] METHOD FOR THE STIMULATION OF THE IMMUNE SYSTEM OF AN ANIMAL BY USE OF LIMULUS TEST-POSITIVE PLANT GLYCOLIPID

[75] Inventors: Gen-Ichiro Soma, 1-10-21, Higashi-Tamagawa Setagaya Ward, Tokyo; Jun Yoshimura; Daisuke Tsukioka, both of Chiba; Den'ichi Mizuno, Okamoto-18, Kamkura City, Kanagawa; Haruyuki Oshima, Hachioji, all of Japan

[73] Assignees: Chiba Flour Milling Co., Ltd., Chiba; Den'ichi Mizuno, Kamakura; Gen-Ichiro Soma, Tokyo, all of Japan

[21] Appl. No.: 990,640

[22] Filed: Dec. 14, 1992

Related U.S. Application Data

[62] Division of Ser. No. 475,890, Feb. 6, 1990, Pat. No. 5,236,709.

[30] Foreign Application Priority Data

Feb. 6, 1989 [JP] Japan .................... 1-25739
Oct. 2, 1989 [JP] Japan .................... 1-255210

[51] Int. Cl.⁶ .............................................. A61K 35/78
[52] U.S. Cl. .................................. 424/195.1; 514/783
[58] Field of Search .................. 424/195.1, 85–92; 435/240–244; 514/783

[56] References Cited

U.S. PATENT DOCUMENTS

| | | | |
|---|---|---|---|
| 1,756,574 | 4/1930 | Takamine | 424/195.1 |
| 2,229,684 | 1/1941 | Supplee | 424/195.1 |
| 3,318,773 | 5/1967 | Fujimaki | 424/155.1 |
| 4,473,647 | 9/1984 | Carpenter | 435/240 |
| 4,863,726 | 9/1989 | Stevens | 424/92 |
| 4,894,227 | 1/1990 | Stevens | 424/85.2 |

Primary Examiner—Michael G. Wityshyn
Assistant Examiner—Ralph Gitomer
Attorney, Agent, or Firm—June M. Bostich

[57] ABSTRACT

A limulus test-positive plant glycolipid having the following properties: molecular weight: 8000 ±1000 by SDS electrophoresis, number of phosphorous not less than 1/mol; number of hexosamine 6 ±2/mol; number of fatty acids 6 ±2/mol is effective in the stimulation of osteogenesis, oviposition and shell strength improvement in animals. The glycolipid may be administered as a composition comprising an effective amount of the glycolipid in admixture with a pharmaceutically or veterinarily acceptable carrier, such that when administered to an animal, the immune system of the animal is favorably stimulated.

11 Claims, 6 Drawing Sheets

FIG. 5
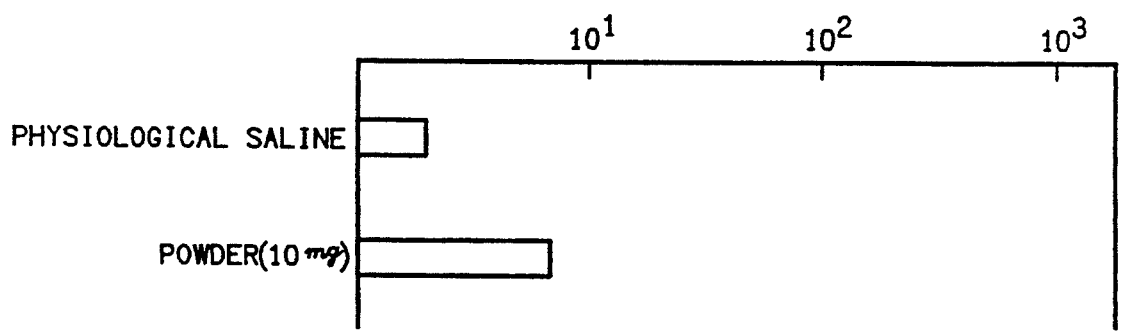
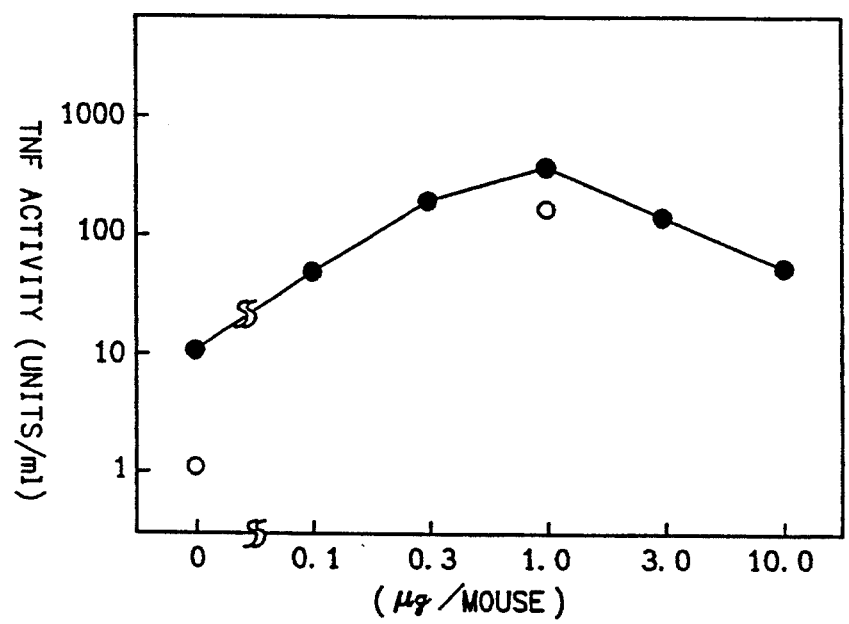
FIG. 6
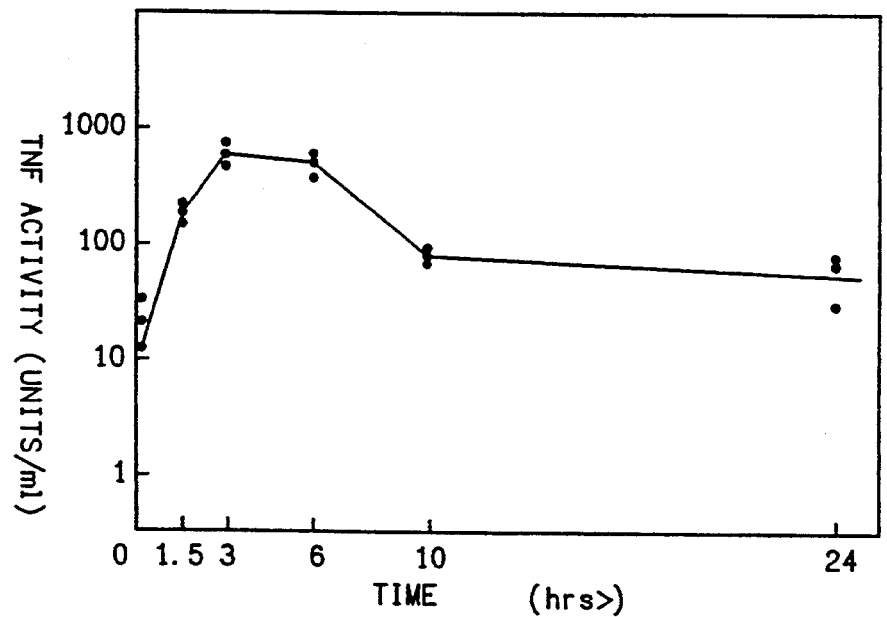
FIG. 7

METHOD FOR THE STIMULATION OF THE IMMUNE SYSTEM OF AN ANIMAL BY USE OF LIMULUS TEST-POSITIVE PLANT GLYCOLIPID

This is a division of application Ser. No. 07/475,890, filed on Feb. 6, 1990, now U.S. Pat. No. 5,236,700.

FIELD OF THE INVENTION

The present invention relates to limulus test-positive plant glycolipid. More particularly, it is concerned with limulus test-positive glycolipid, and a method of stimulating the immuno system of an animal.

DESCRIPTION OF THE PRIOR ART

Organisms have their own immunity to keep their internal conditions from being disturbed by exogenous or endogenous matter and to maintain their homeostasis. Thus, the lowering of immunity causes deterioration of health, occurrence of various diseases, stimulation of aging, etc. On the other hand, its activation leads to improvement of health, prevention against occurrence of various diseases, cure of various diseases and prevention of aging or the like.

For the above-mentioned reasons, it has been desired to provide a substance capable of activating immunity. To date, PSK KRESTIN ® (trademark of Kureha Kagaku Co., for PSK (polysaccharide K) in Japan and registered in Japan). LENTINAN ® (trademark of Ajinomoto Co. for lentinan in Japan and registered in Japan), BESTATIN ® (trademark of Nihon Kayaku Co. for ubenimex in Japan and registered in Japan). SONIFILIAN ® (trademark of Kaken Seiyaku Co. for sizofiran in Japan and registered in Japan), OK-432 [Cancer Chemotherapy Reports Part 1, vol. 58, No.1, p.10, 1972; PICIBANIL ® (trademark name of Chugai Seiyaku Co. for antimalignant streptococcus preparation in Japan and registered in Japan), etc. are known to have such capability.

In addition, publicly known limulus test-positive glycolipid includes E. coli LPS (lipopolysaccharide), B. pertussis LPS and Salmonella LPS, and these are utilized in some experiments; the term "limulus test" will be detailed later.

They are, however, so toxic that their uses have not been realized. Limulus test-positive plant glycolipid has not been found.

Of the prior art immuno stimulators, PSK, Lentinan ®, Bestatin ® and Sonifilan ® immunity stimulators have no TNF productivity, and thus their immuno stimulation is poor.

Surely OK-432 immunity stimulator is known to have TNF productivity, but a rather large quantity of it must be administered to produce a satisfactory quantity of TNF, thereby inevitably causing attack of fever or rigor, lowering of blood pressure, and reduction in the number of thrombocytes. Accordingly, OK-432 immunity stimulator has a low chemotherapeutic coefficient. OK-432 has an additional drawback in that its production steps include culturing of microorganisms, and extremely complicated procedures for its separation and purification with the results of high production costs. Further, OK-432 immunity stimulator fails to produce TNF through oral or subcutaneous administration which is very convenient for medication; therefore OK-432 immunity stimulator must be administered by inconvenient means.

Here, the term "TNF" is the generic name for tumor necrosis factors produced by macrophage (The Journal of Biol. Chem., 260, pp. 2345-2354, 1985), and the production quantity of TNF increases depending on the activity of macrophage. Macrophage is the generic name for large amoeba-like cells which belong to immunocompetent cells, are present in most internal tissues of animals, and prey and digest particulate foreign matter and waste cells in the body. The term "chemotherapeutic coefficient" is the ratio of the maximum tolerant dose of the host to the medicine to the minimum effective dose of the medicine; the larger the ratio is, the better the medicine is.

BRIEF SUMMARY OF THE INVENTION

The present invention is intended to provide limulus test-positive plant glycolipid which is free from the drawbacks of the prior art, and thus has a high degree of immuno stimulation and a large chemotherapeutic coefficient, and further may be produced at a low cost, and may be administered intravenously and orally and may be applied to the skin. Here the "limulus test" is a method invented by Levin in 1968 for quantitative determination of endotoxin using a horseshoe crab haemocyte extract and a chromogenic substrate.

Accordingly, an object of the present invention is to provide limulus test-positive plant glycolipid which has a high degree of immuno stimulation and a large chemotherapeutic coefficient, and further may be produced at a low cost, and may be administered intravenously and orally and may be applied to the skin.

An additional object of the present invention is to provide a method of stimulating the immuno system of an animal.

Further there are provided immuno stimulators, veterinary immuno stimulators, immunity diagnostic reagents, veterinary immunity diagnostic reagents, quasi drugs defined in the Japanese Pharmacopoeia, cosmetics, food and feed comprising at least one member of said glycolipid. Here "comprising at least one member of said glycolipid" is intended to mean that the respective members of the limulus test-positive glycolipid of the present invention may be used individually or may be combined with each other or with any other matter optionally.

In addition, according to the present invention, there is provided an immuno stimulator composition comprising an effective amount of the glycolipid of the present invention in admixture with a pharmaceutically or veterinarily acceptable carrier, such that when administered to an animal, the immune system of said animal is stimulated to effect at least one of osteogenesis, oviposition and shell strength improvement.

BRIEF DESCRIPTION OF THE DRAWINGS

FIG. 5 is a graph demonstrating the endogenous TNF production stimulation of the limulus test-positive plant glycolipid of the present invention when it is administered orally, in comparison with that of a control or one of the prior art immuno stimulators.

FIG. 6 is a graph showing the dose-dependency of the endogenous TNF production stimulation of the limulus test-positive plant glycolipid of the present invention.

FIG. 7 is a graph showing the administration interval-dependency of the endogenous TNF production stimulation of the limulus test-positive plant glycolipid of tile present invention.

DETAILED DESCRIPTION OF THE INVENTION

Figure 1:
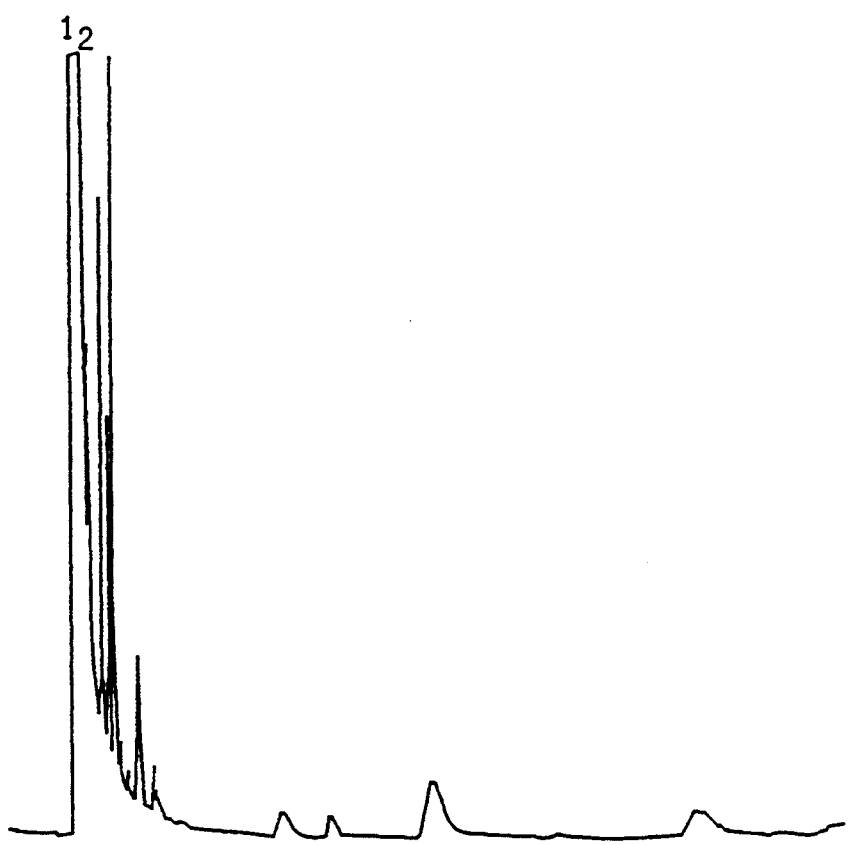
FIG. 1 is a gas chromatographic chart of the limulus test-positive plant glycolipid of the present invention which shows the peaks evidencing the presence of fatty acids in the molecule.

The starting plants available for use in the present invention include all the plants which contain a limulus test-positive ingredient. For example, any plant belonging to Gymnospermae, Monocotyledoneae, Dicotyledoneae, Pteridophyta, Algae or Fungi may be used separately or in admixture with each other.

The plants belonging to Gymnospermae available for use in the present invention include, for example, those belonging to Pinaceae.

Illustrative embodiments of the plants belonging to Monocotyledoneae available for use in the present invention are those belonging to Gramineae, Iridaceae, Zingiberaceae, Araceae or Liliaceae. The plants belonging to Gramineae available for use in the present invention include, for example, rice plant, wheat, barley, rye and oats. Also mixtures of them may be used according to the present invention.

The plants belonging to Dicotyledoneae available for use in the present invention are, for example, those belonging to Rubiaceae, Cruciferae, Cucurbitaceae, Lauraceae, Juglandaceae, Piperaceae, Umbelliferae, Menispermaceae, Saururaceae, Solanaceae, Rosaceae, Actinidiaceae, Leguminosae, Rutaceae, Magnoliaceae or Myristicaceae. These plants may be used separately or in admixture with each other.

The plants belonging to Pteridophyta available for use according to the present invention are, for example, those belonging to Equisetaceae or Osmundaceae. Also these plants may be used separately or in admixture with each other.

As plants belonging to Algae, any one belonging to, for example, Phaeophyceae, Rhodophyceae, Chlorophyceae or Cyanophyceae may be used separately or in admixture with each other. An illustrative embodiment of the plants belonging to Chlorophyceae is chlorella.

As a fungus available for use according to the present invention, for example, any one belonging to Basidiomycetes or Ascomycetes may be used separately or in admixture with each other.

Detection and Determination of the Content of Limulus Test-positive Plant Glycolipid The detection and determination of the content of the limulus test-positive plant glycolipid of the present invention contained in any one of the plants referred to above may be carried out by using, for example, a reagent set commercially available from Sei-Kagaku Kogyo Co. in Japan under the trademark of TOXICOLOR SYSTEM. That is, the starting plant is contacted with LS-1 set of said system, and the chromogenie strength of the plant is determined in comparison with the data of the calibration curve prepared using the Et-2 set of said system.

The limulus test-positive plant glycolipid of the present invention may be separated and purified in such a manner as mentioned below.

Separation and Purification of Limulus Test-positive Plant Glycolipid

1) The starting plant is, if necessary after being sliced, dried and pulverized appropriately, suspended in distilled water, and then the supernatant is collected.

For example, in case the starting plant is supplied in the form of cereal seeds, then the seeds are, if necessary or desired, after the removal of the seed coats, somewhat crushed or pulverized to an edible particle size of powders. The resulting powders are prepared as a dispersion by addition of water thereto, and stirred. The dispersion is allotted to stand or subjected to centrifugation to remove the sediment, or the dispersion is worked into a dough by kneading, and is gently washed with water in a mixer to remove the sediment.

When the above extraction is effected, there is no need to put limitations on the particle size of the seeds, the temperature, the properties and the quantity of the water, the speed and the time of the stirring and the centrifugation conditions. For convenience only, however, the temperature of the water for the extraction is desired to be not more than 50° C. so that the starch in the cereal seeds is not gelatinized. In addition, though the quantity of the water to be added changes depending on the type and the particle size of the cereals used, for easiness of operation only, it is desired to be 20–50 w/v %. At the end of this stage of operation, the purity of the limulus test-positive plant glycolipid of the present invention increases to about 30-fold value in the case of wheat seeds judging from the limulus test activity data.

2) In order to get higher purity, the supernatant may be subjected to ultrafiltration in the conventional manner to remove fractions having molecular weights of 5,000 or less.

3) The resulting dried sample is then suspended in distilled water to a proportion of 50 mg/ml after which it is subjected to centrifugation to collect the supernatant.

4) The supernatant from the above 3) is cooled on ice water, and then an acid added thereto to produce sediment. Here, no specific acid is required, and, for example, trichloroacetic acid (hereunder referred to as TCA only), perchloric acid, trifluoroacetic acid, acetic acid or dichloroacetic acid may be employed.

5) Then the mixture is subjected to centrifugation to collect the sediment which is then washed with distilled water, and then is subjected to centrifugation again to collect the sediment.

6) The sediment from the above 5) is suspended in distilled water, and an alkali is added to the suspension until the sediment dissolves therein. Here, no specific alkali is required, and sodium hydroxide, potassium hydroxide, ammonia, sodium carbonate, sodium acetate or the like may be used. Here, care should be taken that the basicity of the suspension does not go over pH 11 when the sediment dissolves in order to keep the object glycolipid from being deactivated.

7) Then an acid is added to the suspension to bring its pH to pH 8 followed by warming to 37° C. Further addition of an acid makes the suspension basic to produce sediment which is then collected by a centrifuge warmed at 37° C.

8) The thus collected supernatant is cooled on ice, and then subjected to centrifugation at 4° C. again.

9) The supernatant is collected, and then neutralized by the addition of an alkali, and concentrated by ultrafiltration in the conventional manner. Here, no specific alkali is required.

10) Then the concentrate is subjected to gel filtration in the conventional manner, and limulus test-positive fractions are collected and combined. Here, the support for the gel filtration may be, for example, SEPHADEX G-75, G-100, SEPHACRYL S-200, SEPHAROSE 6B (the foregoing are all manufactured by Pharmacia Inc. in U.S.), BIOGEL P-100 (manufactured by Biorad Inc.), TOYOPEAL HW-50, HW-55 (manufactured by Toyo Soda Kogyo Co. in Japan) gel filtration media, or the like. The buffer solution may be any one as long as it can keep the pH within the range of 3–10. For example, Tris-HCl or phosphate buffer solutions may be used.

11) Then a proteolytic enzyme is added to tile combined fractions which are then incubated at 37° C. for 2 or more hours to decompose the remaining proteins. The thus treated solution is then concentrated by ultrafiltration in the conventional manner. Here, no specific proteolytic enzyme is required, and, for example, V8 protease, chymotrypsin, trypsin or thermolysin may be used separately or in optional combinations thereof. The commercially available proteolytic enzymes which may be used according to the present invention include, for example, PRONASE® (Kaken Kagaku Co. in Japan) and PROTEINASE® proteolytic enzyme (Merc Co. in U.S.)

12) Then the collected fractions are treated conventionally, for example, by being subjected to ion-exchange chromatography using MONO Q SEPHAROSE or Q SEPHAROSE high performance ion exchange gel comprising SEPHAROSE ion exchange beads of agarose manufactured by Pharmacia Inc., to collect the limulus test-positive fractions.

13) Then, the fractions are subjected to gel filtration conventionally to collect the desalted limulus test-positive fractions.

By the above-mentioned procedures, in case of wheat seeds, about 20% of the originally present limulus test-positive matter was recovered, and a purified sample of about 95% purity was obtained. This value achieved in the case of wheat seeds is about 1,000 times as high as that obtained at the end of 1) referred to above.

Physical Properties of Limulus Test-positive Plant Glycolipid

As will be explained in detail in the examples given later, the 96% purity sample of the limulus test-positive plant glycolipid of the present invention has a molecular weight of about 8,000 ±1,000 (on SDS electrophoresis), the number of phosphorus of one or more per molecule, the number of hexosamine of 6 ±2 per molecule, and the number of fatty acid of 6 ±2 per molecule.

Forms Supplied

The limulus test-positive plant glycolipid of the present invention may be supplied as such, or in the forms diluted to an optional desired degree. In addition, in order to improve its stability, it may be supplied as dried powders in the conventional manner including lyophilization and spray drying. Each of these forms may be produced conventionally.

Determination of Immuno Stimulation

The immuno stimulation of the limulus test-positive plant glycolipid of the present invention has been confirmed by endogenous TNF production stimulation, endogenous TNF productivity, carbon removal activity and stimulation of osteogenesis, oviposition and shell strength improvement through stimulation of macrophage activity.

Endogenous TNF Production Stimulation and Endogenous TNF Productivity

Carswell et al. report that priming and triggering steps are necessary to produce endogenous TNF in the body of an animal; see Proc. Natl. Acad. Sci. USA., 72, pp. 3666–3670, 1975. Thereafter, many candidate chemicals were tried to stimulate the respective steps. The chemical used to start the priming step is a primer (endogenous TNF production stimulator), while that administered to start the triggering step is a trigger (endogenous TNF productive agent). The limulus test-positive plant glycolipid of the present invention works as both a primer and a trigger as excellent as PICIBANIL ® antimalignant streptococcus preparation, one of the medicines whose usefulness has already been established.

The TNF activity is determined, as follows, on the basis of the cytotoxicity to L929 cells (*Proc. Natl. Acad. Sci. U.S.A.*, 72, PP. 3666–3670, 1973). L-929 cells are cultured in Eagles' Minimum Essential Medium (hereunder referred to only as MEM) with 5% fetal calf serum (hereunder referred to only as FCS) added thereto until 100 ul of the medium contains $8 \times 10^4$ cells, and then the cells are grown in a flat-bottomed plate having 96 wells.

The growth conditions are 37° C. in the presence of 5% $CO_2$, and under a humidity of 100% for 2 hours, and the procedures may be the same as for the conventional cell culture. Then actinomycin D is added to the medium to a final concentration of 1 $\mu$g/ml, and the volume of the culture solution is adjusted to 150 $\mu$l. Immediately thereafter 50 ul of the sample diluted appropriately with MEM medium is added to the culture solution. Here, $ED_{50}$ may be determined by adjusting the dilution appropriately. The L-929 cells having a final volume of 200 82 l are cultured for an additional 18 hours under the same conditions as described above.

In order to determine the cell necrosis activity, first the whole medium is removed followed by addition of a 1% methyl alcoholic solution containing 0.1% crystal violet for fixation staining. Crystal violet stains all the eukaryotic cells, but the dead cells are removed off from the bottom of the flask only by washing after the staining; so the cell necrosis activity may be determined directly. The staining degree is measured on the basis of adsorption at $OD_{590\ nm}$, and is compared with that of a control to determine the cell necrosis activity. This activity is defined as follows.

The dilution of the sample which allows 50% of the L-929 cells to survive (N) is determined. Rabbit TNS is used as the control, and its activity n (units/ml) is determined using $2.4 \times 10^6$ units/mg/mg of TNF-α. The dilution which provides $ED_{50}$ of rabbit TNS is determined.

The activity of the sample (units/ml) is calculated by the equation $N/C \times n$.

Carbon Removal Activity

It has been known for a long time that removal of colloidal carbon from the blood is an indication of macrophage activity (No. 5 of a library of bacteriological technology. "Functions of macrophage and methods of determing them", edited by Board of educatioin of Japanese society for bacteriology, p. 98, published by Saikon Shuppan Co. in Japan in 1985). Thus, the immuno stimulation of the limulus test-positive plant glycolipid administered subcutanously is determined on the basis of the removal rate of the carbon administered intravenously as an indication according to the method described on pp. 1531-1532 of August issue of Cancer Research, 28, 1968.

Stimulation of Osteogenesis

This stimulation was confirmed by an osteolast activation test.

Osteoclast cells are those in charge of absorbing bony tissue which destroy old bones in said tissue. Activation of osteoclast causes activation of osteoblast compensatively thereby making osteogenesis superior to bony adsorption. As a result, the osteogenesis is presumed to be stimulated.

In the osteoclast activation test, parietal bones of fowl's embryo are used as experimental samples. That is, the parietal bones of fowl's embryo are labelled with $^{45}Ca$, and are cultured in a medium containing a medicine candidate (treated group) or in a said candidate-free medium (control group), and thereafter the quantity of the $^{45}Ca$ remaining in the bones and that of the $^{45}Ca$ leaked into the medium during culture are determined. The $^{45}Ca$ leakage rates in both tile treated and control groups are calculated according to the following equation:

$^{45}Ca$ leakage rate=(Quantity of $^{45}Ca$ leaked)/(Quantity of remaining $^{45}Ca$+Quantity of $^{45}Ca$ leaked)

The effect of the candidate is expressed by the following T/C rate:

T/C rate=(Quantity of $^{45}Ca$ leaked in the treated group)/(Quantity of $^{45}Ca$ leaked in the control group)

Theoretically, the values of the T/C rate over 1 mean that the candidate has the expected effect. Here, one of the two parietal bones of embryo from the same fowl was used in the control group, while the other, in the treated group, thereby avoiding influence due to difference in the fowl tested.

Stimulation of Oviposition and Shell Strength Improvement

The captioned activities are confirmed by determining the count of the eggs layed by the fowls with the limulus test-positive plant glycolipid of the present invention administered thereto and the shell strength of the eggs.

Distribution of eggs are under control of notifications of the permanent vice-minister of the Japanese Ministry of Agriculture and Forestry. According to the existing notification of No. Rev. 54-Tiku-A-5136 dated Dec. 25, 1979, eggs are classified in view of their weights and the results of tests on their appearance and transmittance. But no reference is made therein to shell strength which can be an indication to prevent breakages of eggs during carrying, handling, use, etc. The notification states only that the outer compartment must have a value of 8.8 or more when tested according to JIS (Japanese Industrial Standards) first class rupture strength standard. But, even if the outer compartment is very stout, no doubt the breakages of eggs because of vibration during carrying or holding cannot be prevented. Therefore, there are not a few cases where only eggs having a shell strength over a certain level are bought by large users such as restaurants or supermarkets. In such cases, strength of $4\ kg/cm^2$ is deemed to be satisfactory.

Up to now, substances, feeds or the like being effective to increase egg shell strength have been neither developed nor sold.

Uses of the Limulus Test-positive Plant Glycolipid

The limulus test-positive plant glycolipid of the present invention has various uses.

The first reason for the various uses resides in that the starting material is consumed by animals including human beings, and thus there are no problems awaiting solution when the glycolipid is administered to animals including human beings.

The second reason resides in that the limulus test-positive plant glycolipid of the present invention may be supplied in various forms, because it may be supplied as such or as diluents diluted to optional degrees or as dried powders.

The third reason resides in that the limulus test-positive plant glycolipid of the present invention is cheap.

One of the uses of the limulus test-positive plant glycolipid of the present invention having the advantages mentioned above is an immuno stimulator or a veterinary immuno simulator wherein the immuno stimulation is utilized directly.

As the second use, the limulus test-positive plant glycolipid of the present invention may be made into immunity diagnostic reagents or veterinary immunity diagnostic reagents for checking immuno conditions of animals including human beings on the basis of the immuno stimulation.

The third use of the limulus test-positive plant glycolipid of the present invention includes quasi drugs defined in the Japanese Pharmacopoeia, cosmetics, foods, feeds, etc. with the limulus test-positive plant glycolipid of the present invention incorporated therein to induce immuno stimulation. For example, cosmetics with the limulus test-positive plant glycolipid of the present invention are useful to prevent aging of the skin and to stimulate metabolism and thus to keep the skin fresh for a long time.

Processes for Producing the Preparations Supplied

Any of the above preparations including immuno stimulators may be produced conventionally. For example, in the conventional manner of preparing medicines or veterinary medicines, immuno stimulators and veterinary immuno stimulators may be supplied in the form of oral, intravenous or intramuscular preparations containing the limulus test-positive plant glycolipid only or in admixture with other substances. Further, many macrophages are present on the skin, so the limulus test-positive plant glycolipid of the present invention may be prepared as skin ointments in order to obtain better effects.

Hereunder, the present invention will be explained in detail with reference to examples and experiments.

EXAMPLE 1

1) In a small kneeder, there was charged 3,120 9 of hard flour containing 1.09% of ash (Hard Red Spring wheat from U.S.A. or Canada) followed by addition of 2.03 l of distilled water thereto and kneading for 10 minutes to prepare a dough. The mixture was allowed to stand for 15 minutes, and then 10 l of water was added to the mixture followed by gentle stirring to extract a starch emulsion and to dissolve soluble ingredients in the water. The resulting solution was allowed to stand in a refrigerator at 5° C. for 12 hours, and then the sediment containing starch etc. was removed. The supernatant was lyophilized to get 201.1 g of powders (Powder A).

Then 5 l of distilled water was added to the residual dough followed by gentle stirring, and the mixture was treated in the same manner as the above to get 40.1 g of powders (Powder B).

2) The powders A and B were charged in an ultrafilter HF-Lab1 (Amicon Co.), and the ultrafiltration was carried out using a hollow cartridge HF-Lab1PM5 for fractions having a molecular weight of 5,000, and another hollow cartridge HF-Lab1PM10 for fractions having a molecular weight of 10,000; the temperature range was 5°–10° C., the inlet pressure was 25 p.s.i. (1.76 kg/cm$^2$), and the outlet pressure was 15 p.s.i. (1.06 kg/cm$^2$). As a result, the respective fractions were named as follows:

Powder A: Fractions having a molecular weight of 5,000 or less were named $a_1$.
 Fractions having a molecular weight of 5,000 or more were named $a_2$.
Powder B: Fractions having a molecular weight of 5,000 or less were named $b_1$.
 Fractions having a molecular weight of 5,000 or more were named $b_2$.
Powder A: Fractions having a molecular weight of 10,000 or less were named $a_3$.
 Fractions having a molecular weight of 10,000 or more were named $a_4$.
Powder B: Fractions having a molecular weight of 10,000 or less were named $b_3$.
 Fractions having a molecular weight of 10,000 or more were named $b_4$.

Each of these fractions was subjected to the limulus test according to the method detailed in Experiment 1 given later, and it was confirmed that much limulus test-positive ingredients are present in fractions having a molecular weight of 5,000 or more, whereas little limulus test-positive ingredients are present in fractions having a molecular weight of 5,000 or less.

3) Thirty grams of the above powder $a_2$ was placed in a 1 l Erlenmeyer flask after which 600 ml of distilled water was poured thereon. The resulting mixture was stirred with a stirrer for 60 minutes, and then subjected to centrifugation at 10,000 g for 10 minutes using a Hitachi cooling type high speed centrifuge SCR-20B (the rotor RPR16 was cooled to 4° C. beforehand) to recover the supernatant.

4) The supernatant from the above 3) was placed in another 1 l Erlenmeyer flask followed by dropwise addition of 20.5 ml of a 100% aqueous solution of TCA cooled to 2° C. beforehand while cooling on ice (the temperature of the solution was about 2° C.) and stirring with a stirrer. After the completion of the dropwise addition, the flask was allowed to stand in ice water for 10 minutes.

5) Next, the mixture was subjected to centrifugation (at 10,000 g for 10 minutes) at 4° C. in the same manner as the above to collect sediment which was in turn put in a 500 ml beaker to,tether with 300 ml of distilled water while cooling in ice water to prepare a suspension. The resulting suspension was cooled in ice water and subjected to centrifugation (at 10,000 g for 10 minutes) at 4° C. in the same manner as the above to recover sediment.

6) The sediment was placed in a 1 l beaker followed by addition of 500 ml of distilled water to prepare a suspensions. The resulting suspension was neutralized to pH 7 by the use of about 3.5 ml of 1N sodium hydroxide, and then, while cooling in ice water, about 2 ml of 1N sodium hydroxide was added to the neutralized suspension until a 0.02N sodium hydroxide solution is prepared to dissolve the sediment.

7) About 1.5 ml of 1N hydrochloric acid was added to the solution to bring the pH to 8 followed by addition of 100 ml of distilled water. The solution was transferred to a 1 l Erlenmeyer flask which was then shaken slowly in an incubator at 37° C. for 30 minutes.

8) The solution from the above 7) was mixed with 30 ml of a 100% aqueous solution of TCA, and then slowly shaken in an incubator at 37° C. for 10 minutes. Thereafter the solution was subjected to centrifugation at 3,000 g for 10 minutes using a centrifuge, Tomy CD100R (Tomy Seiki Co. in Japan)

9) The supernatant was collected and cooled on ice, and then subjected to centrifugation at 4° C. (at 10,000 g for 10 minutes.)

10) The supernatant was collected and neutralized to pH 7 with about 3.6 ml of 10N sodium hydroxide, and the neutralized solution was concentrated using an ultrafilter (Toyo Roshi UHP-150, Filter:UK-10, N$_2$ pressure: 4.0 kg/cm$_2$)

11) The resulting concentrate (60 ml) was subjected to gel filtration (buffer: 10 mM Tris-HCl/10 mM NaCl (pH 7.5), flow speed: 60 ml/h.) to collect 20 ml fractions using SEPHAROSE 6B anion exchanger column (manufactured by Pharmacia Inc., column size: 5 cm (i.d.)×100 cm (2 l)).

12) The 43rd to 56th fractions were combined to prepare 280 ml of a solution followed by addition of 450 μg of PRONASE ® proteolytic enzyme E (Kaken Kagaku Co. in Japan) and warmed at 37° C. for 2 hours while shaking. Thereafter the mixture was concentrated using an ultrafilter (Toyo Roshi UHP-62, filter: UK-10. N$_2$ pressure: 4.0 kg/cm$_2$). Then the concentrate was subjected to anion exchange chromatography using FPLC system (manufactured by Pharmacia Inc., column: mono g HR 10/10). That is, the sample was applied to the column using a buffer solution containing 10 mM Tris-HCl (pH 7.5) and 10 mM of NaCl, and then the column was washed with 200 ml of a liquid containing 165 mM of NaCl in addition to the components of the above buffer solution. Then, totally 400 ml of the eluate was used to elute the object glycolipid while increasing the NaCl concentration so that the NaCl concentration gradient ranges from 165 mM to 1M. Two ml fractions were collected. The 5th to 8th fractions after the start of the concentration gradient which were confirmed to be positive to the limulus test were combined to yield 8 ml of glycolipid of about 92% purity (glycolipid: 3.03 mg (in terms of *E. coli* LPS according to the limulus test; the same applies to the following), sugar: 0.23, protein: 0.04)

13) Then, the 8 ml was subjected to gel filtration (buffer: water) using SEPHADEX G-25 gel filtration media (column: 2.0 cm (i. d.×20.2 cm (66 ml)) to collect 3 ml fractions. The 9th to 12th fractions confirmed to be positive to the limulus test were combined to yield 12 ml of glycolipid of about 95% purity (glycolipid: 2.7 mg, sugar: 0.18, protein: 0.0:3). The sugar content was determined according to the phenol—sulfuric acid method, while the protein content, according to the Lowry method. Here, the combined fractions were confirmed to be acidic by anion exchange chromatography. The molecular weight according to SDS electrophoresis was 6,000–10,000.

14) The above fractions were frozen at −80° C., and then lyophilized to a constant weight which was measured to be 0.75 mg. Hereunder, this lyophilized sample is referred to as CHF only.

The limulus activity of this CHF were determined to be 2.7 mg according to the method described in Experiment 1 given later, so its specific activity is calculated to be 3.6 (2.7÷0.75). Here, the foregoing purification procedures are supposed to have removed substantially all the independent sugars present as contaminants, so all the sugars detected are supposed to be those constituting the glycolipid CHF. Thus, the purity of CHF on the basis of weight at this stage may be calculated as follows:

Protein content: 0.03 mg
Glycolipid content: 0.72 mg (0.75−0.03)
Purity=0.72÷0.75×96 (%)

Physical properties of CHF

15) Molecular weight

CHF was dissolved in distilled water to prepare a 1 mg/ml solution of CHF, and 4 μl of the solution was placed in a 1.5 ml Treff tube. Separately, 2.5% of SDS, 5% of mercaptoethanol and 10 mM Tris—HCl (pH8.0) were added to 1 mM EDTA to prepare 1 μl of an SDS treatment solution, and this solution was added to the above solution in the Treff tube which was then dipped in boiling water for 3 minutes. Phast System of Pharmacia Inc. was used in the electrophoresis experiments. That is, one μl of the mixture was applied to a gel (Phast Gel Gradient 8–25 of Pharmacia Inc.) which was connected to the electrodes through SDS-Buffer Strip of Pharmacia Inc., the maximum potential difference and the maximum electric current were set to 250 v and 10 mA, respectively, and then the electrophoresis started. At the end of the electophoresis, the behaviors in Coomassie staining and silver staining were observed.

For Coomassie staining, Phast Gel Blue R was used as the staining solution, and a mixture of methanol, acetic acid and distilled water (volumetric ratio is 3:1:6), as the decoloring solution. The staining and decoloring were carried out in the following order:

1) Stained at 50° C. for 8 minutes.
2) Stained at 50° C. for 5 minutes.
3) Stained at 50° C. for 8 minutes.
4) Decolored at 50° C. for 10 minutes.
5) Protected at 50° C. for 5 minutes (a mixture of glycerol, acetic acid and distilled water in a volumetric ratio of 5:10:85).
6) Dried.

The silver staining was carried out in the following order:

1) Treated with a wash (a mixture of ethanol, acetic acid and distilled water in a volumetric ratio of 5:1:4) at 50° C. for 2 minutes.
2) Treated with a wash (a mixture of ethanol, acetic acid and distilled water in a volumetric ratio of 10:5:85) at 50° C. for 2 minutes.
3) Treated with a wash (a mixture of ethanol, acetic acid and distilled water in a volumetric ratio of 10:5:85) at 50° C. for 4 minutes.
4) Treated with a sensitizer solution (8.3% glutar dialdehyde) at 50° C. for 6 minutes.
5) Treated with a wash (a mixture of ethanol, acetic acid and distilled water in a volumetric ratio of 10:5:85) at 50° C. for 3 minutes.
6) Treated with a wash (a mixture of ethanol, acetic acid and distilled water in a volumetric ratio of 10:5:85) at 50° C. for 5 minutes.
7) Treated with a wash (deionized water) at 50° C. for 2 minutes.
8) Treated with a wash (deionized water) at 50° C. for 2 minutes.
9) Treated with 0.25 w/v % of silver nitrate at 40° C. for 13 minutes.
10) Treated with a wash (deionized water) at 30° C. for 30 seconds.
11) Treated with a wash (deionized water) at 30° C. for 30 seconds.
12) Treated with a developer (0.04 v/v % of formaldehyde+2.5 w/v % of sodium carbonate as a wash) at 30° C. for 30 seconds.
13) Treated with a developer (0.04 v/v % of formaldehyde+2.5 w/v % of sodium carbonate as a wash) at 30° C. for 4 minutes.
14) Treated with a reaction termination solution (5 v/v % of acetic acid) at 50° C. for 2 minutes.
15) Treated with a protective solution (a mixture of acetic acid, glycerol and distilled water in a volumetric ratio of 10:8:85) at 50° C. for 3 minutes.
16) Dried Glycolipid are subjected to silver staining, but not to Coomassie staining. This difference was taken into consideration to observe the stained bands, and the main stained band of CHF was found at a position indicating a molecular weight of 8,000 ±1,000. Similarly, the stained bands of *E. coli* LPS were observed to be successive in tiers, and the molecular weight of the stained band having the highest staining strength was estimated to be 30,000 ±5,000. In the case of *B. pertussis*, the stained bands having the highest staining strength were observed at places indicating molecular weights of 6,000 ±1,000 and 9,000 ±1,000.

16) Phosphorus Content

The captioned content was determined as follows according to the Chen-Toribara method (Chen et el., "Analytical Chemistry", vol. 28, pp. 1756–1758, 1956)

CHF was dissolved in distilled water to prepare 20 μl of a solution containing 25 μg of CHF which was then placed in a small test tube. To the mixture there was added 20 μl of 50 v/v % perchloric acid, and then the mixture was heated on a gas burner for 1 minute to ash. Thereafter, 0.5 ml of distilled water and then 0.5 ml of a reaction reagent (a portion of the preparation made by mixing 1 ml of 6N sulfuric acid, 2 ml of distilled water, 2 ml of 2.5 v/w % ammonium molybdate and 1 ml of 10 v/w % of ascorbic acid) were added to the heated mixture which was then allowed to stand for 30 minutes at room temperature. Thereafter the absorption at 820 nm ($OD_{820\ nm}$) was determined. Here, as the standard sample for the preparation of the calibration curve, potassium didrogen phosphate (manufactured by Wako Jun-yaku Co. in Japan) was diluted with water to prepare 0.5 ml of solutions containing 2.5 μg, 1 μg, 0.25 μg or 0 μg of the standard in terms of phosphorus. In this connection, 1 g of phosphorus corresponds to 4.39 g of potassium didrogen phosphate. The effects observed are shown in Table 1 given below.

TABLE 1

| $OD_{820nm}$ | Samples |
|---|---|
| | Potassium dihydrogen phosphate (in terms of phosphorus; μg) |
| 0.002 | 0 |
| 0.150 | 0.25 |
| 0.620 | 1.0 |
| 1.559 | 2.5 |
| | CHF (data of four samples) (content of phosphorus calculated considering calibration curve; μg) |
| 0.036 | 0.1 |
| 0.073 | 0.2 |
| 0.104 | 0.3 |
| 0.139 | 0.4 |

Note: The data of CHF are modified by subtracting the values of the control not subjected to the heating from the observed values in order to avoid occurrence of errors due to mixing-in of inorganic phosphorus from, for example, phosphate buffer solution.

On the assumption that the molecular weight of CHF is 8,000, the number of phosphorus in CHF is calculated to be 1–4 per mol. according to the following equation on the basis of the data shown in the above table.

$$\text{Phosphorus content} \times 10^{-6} \times \frac{\text{Molecular weight}}{25 \times 10^{-6}} \times \frac{1}{32}$$

For an explanation as to why the number of phosphorus ranged from 1 to 4, one may guess that the phosphoric acid(s) may be eliminated due to the mixing-in of the monophosphoesterase in the purification stage.

Similarly, the number of phosphorus of *E. coil* LPS (molecular weight was assumed to be 30,000) and *B. pertussis* LPS (molecular weight was assumed to be 8,000) were determined to be about 12 and 5 per mol., respectively.

17 ) Hexosamine Content

The captioned content was determined as follows according to the Elson-Morgan method (Library of biochemical experiments, No. 4, pp. 377–379, Tokyo Kagaku Dojin Shuppan Co. in Japan).

CHF was dissolved in distilled water to prepare a solution containing 1 mg/ml of CHF, and its 100 μl portion was placed in a test tube with a screwcap (manufactured by Iwaki Glass Co. in Japan) followed by addition of 100 μl of 8N HCl thereto, and the mixture was heated at 110° C. for 16 hours, and then about 200 μl of 4N NaOH was added to the mixture to bring the pH to 7. A 100 μl portion of the mixture was separated off and placed in another test tube with a screwcap followed by addition of 200 μl of Reagent A explained below thereto. The mixture was then heated at 105° C. for 1.5 hours, and then cooled with a running water. Next, a 100 μl portion of the mixture was separated off followed by addition of 670 μl of a 96% ethanol and then 67 μl of Reagent B explained below, and was then allowed to stand at room temperature for 1 hour followed by determination of adsorption at 535 nm. As the standard sample to prepare the calibration curve, 0.20–200 μg/ml of N-acetyl glucosamine (Wako Jun-yaku Co. in Japan) was used.

Reagent A: prepared by mixing 75 μl of acetyl acetone and 2.5 ml of 1.25N sodium carbonate Reagent B: prepared by mixing 1.6 g of p-dimethyl benzaldehyde, 30 ml of conc. hydrochloric acid and 30 ml of 96% ethanol As a result, the number of the hexosamine in CHF was 6 ±2 per mol. on the assumption that its molecular weight is 8,000. Similarly, the number of the hexosamine in *E. coli.* LPS (molecular weight was assumed to be 30,000) and *B. pertussis* LPS (molecular weight was assumed to be 8,000) were determined to be 45 ±6 and 16 ±2 per mol, respectively.

17) Fatty Acid Content

To 90 μl of a solution of CHF in distilled water containing 1 mg/ml of CHF there was added 10 μl of an internal standard (0.55 mM margaric acid) followed by addition of 1.0 ml of 0.5M sodium methylate for hydrolysis and esterification of fatty acid esters. The mixture was allowed to stand at room temperature for 1 hour followed by the addition of 960 μl of 0.5N HCl thereto for neutralization. Two ml of hexane was added to the mixture which was then stirred vigorously for 15 minutes. Next, the resulting mixture was subjected to centrifugation at 1,000 g for 5 minutes to separate off the hexane layer. The hexane was evaporated off by nitrogen gas, and the layer was concentrated to about 20 μl. The resulting concentrate was subjected to gas chromatography (GC8APF manufactured by Shimazu Co. in Japan; capillary column: FSCAP Sp2330 manufactured by Spelco Co. in Canada; carrier gas: nitrogen) to determine the fatty acid content. As the standard for determination of the fatty acid content, there was used *E. coli* type LA-15-PP, a synthetic lipid A manufactured by Dai-ichi Kagaku Yakuhin Co. in Japan and known to have a molecular weight of 2,000 and a fatty acid count of 6 per mol.

As a result, the number of the fatty acid in CHF was 6 ±2 per mol. on the assumption that its molecular weight is 8,000.

Similarly, the number of the fatty acid in *E. coli.* LPS (molecular weight was assumed to be 30,000) and *B. pertussis* LPS (molecular weight was assumed to be 8,000) were determined to be 18 and 15 per mol, respectively.

Figure 2:
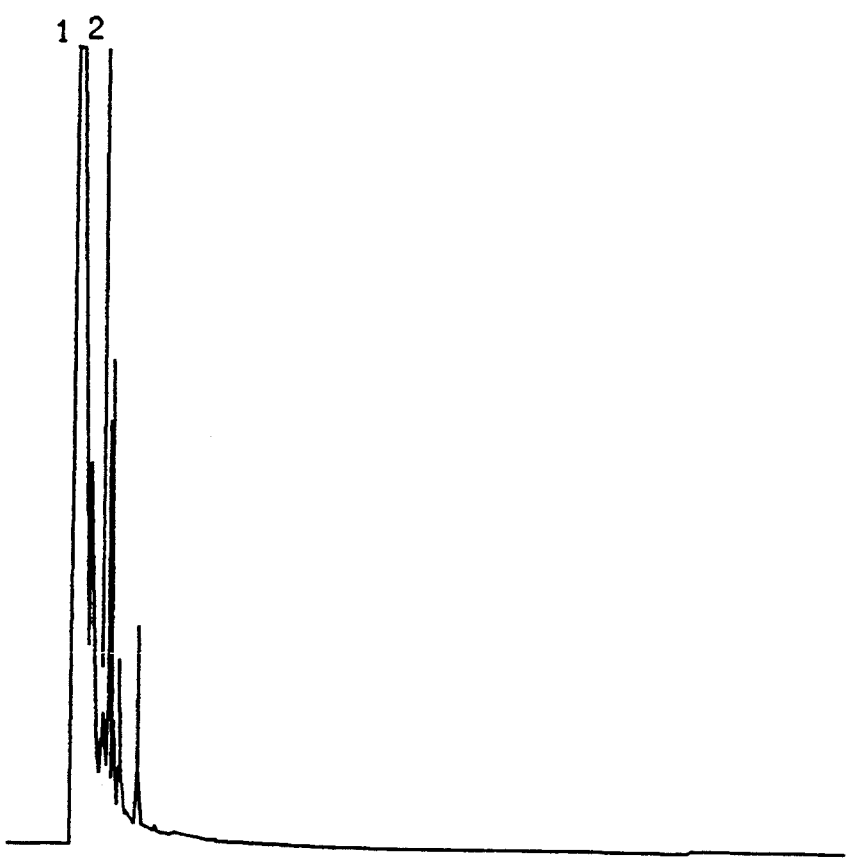
FIG. 2 is a gas chromatographic chart of E. coli LPS which shows the peaks evidencing the presence of fatty acids in the molecule.
Figure 3:
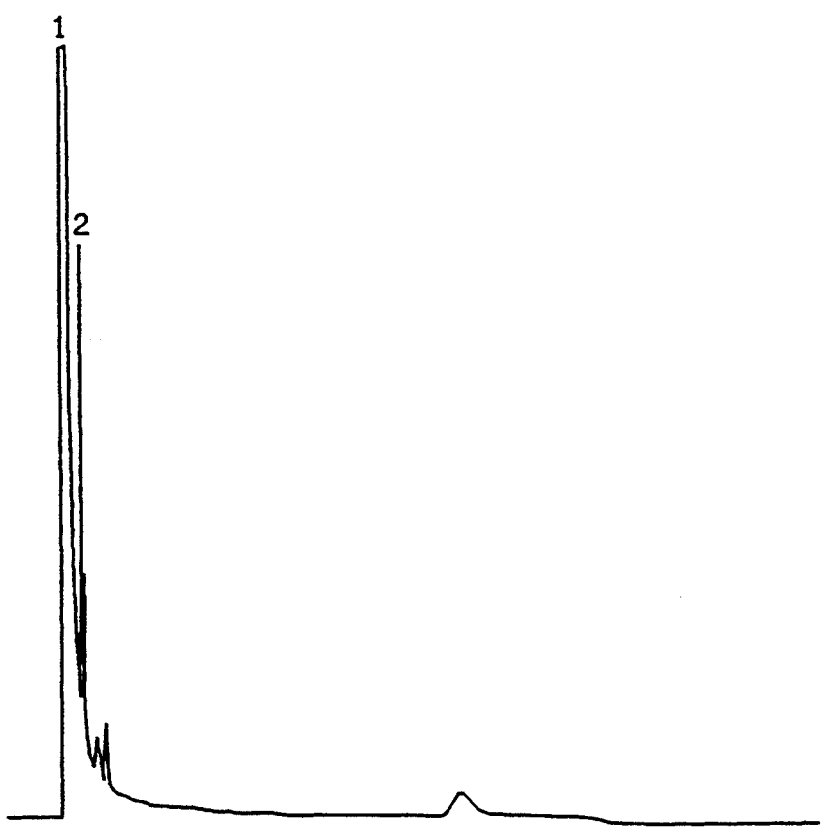
FIG. 3 is a gas chromatographic chart of B. pertussis LPS which shows the peaks evidencing the presence of fatty acids in the molecule.

The charts observed in the above gas chromatography are shown in accompanying FIGS. 1–3. FIG. 1 is the chart of CHF, FIG. 2 is that of *E. coli* LPS, and FIG. 3 is that of *B. pertussis* LPS.

The retention times (minutes) corresponding to the main peaks shown in FIGS. 1–3 are as follows:

| | No. of peak | Retention time (min.) |
|---|---|---|
| FIG. 1: | 1 | 2.450 |
| | 2 | 2.758 |

-continued

|  | No. of peak | Retention time (min.) |
|---|---|---|
| FIG. 2: | 1 | 2.417 |
|  | 2 | 2.742 |
| FIG. 3: | 1 | 2.433 |
|  | 2 | 3.028 |

By the comparison of FIGS. 1-3, it is apparent that CHF and *E. coli* LPS show similar charts, whereas the chart of CHF is clearly different from that of *B. pertussis* LPS.

Experiment 1: Quantitative Determination of Limulus Test-positive Plant Glycolipid The quantitative determination of limulus test-positive plant glycolipid contained in various plants was carried out using TOXICOLOR SYSTEM commercially available from Sei-Kagaku Kogyo Co. in Japan.

1) Distilled water for injection was poured in a flat- or round-bottomed plate having 96 wells in a proportion of 180 μl per well. Twenty μl of the test sample (when the sample is a solid, it is dissolved in distilled water for injection) was placed in one of the wells of the plate. Pipetting was effected while stirring with a plate mixer to prepare a ten-fold dilution; hereafter, 20 μl portions of the respective diluted samples may be collected successively to prepare ten-fold serial dilutions including 100-fold, 1000-fold and so on. In addition, the degree of dilution may be changed as desired by adjusting the quantitative rate of the distilled water for injection to the sample.

2) As the internal standard, a 100,000-fold dilution of a solution containing 1.5 μg/ml of *E. coli* was prepared and used to confirm that the dilution process and the chromogenic behaviors of the limulus test were normal.

3) Thirty-five μl of the ten-fold dilution mentioned in the above 1) placed in a well of another plate followed by addition of 35 μl of LS-1 set of TOXICOLOR SYSTEM commercially available from Sei-Kagaku Kogyo Co. in Japan. The mixture was allowed to stand at 37° C. for 30 minutes, then 105 μl of 1M aqueous acetic acid was added to the mixture to terminate the reaction. The absorbance of this sample solution was determined at a wave length of 415 nm using Plate Reader MTP-100, an absorbance meter for 96 wells manufactured by Corona Denki Co. in Japan. Distilled water was used as the background, and 42 pg/ml of the ET-1 set of the TOXICOLOR SYSTEM of Sei-Kagaku Kogyo Co. in Japan was used to prepare a calibration curve. This calibration curve was used as the basis to determine the quantity of the limulus test-positive plant glycolipid of the respective test samples; the absorbance of distilled water was assumed to be 0.

Here, the experiments were carried out again at other dilutions when the value did not come within a range of 10-45 pg/ml because the chromogenic strength was confirmed to depend on the content of the limulus test-positive plant glycolipid within said range in the case where the above-mentioned LS-1 set was used.

The quantitative determination of the diluted sample was calculated according to the following equation:

(the value determined on the calibration curve)×(the degree of dilution)

The results of the experiments are shown in Table 2 where solid samples are reported in units of ng/g, and liquid samples, in units of ng/ml.

In the table, the companies and places referred to in the column of samples, are the suppliers and growing districts of the respective samples. Samples without such referring-to were bought at the Nakano-cho branch of the super store Chujitsuya located in Tsukui-gun in Kanagawa, Japan, and their makers could not be identified.

TABLE 2

| Sample (solid) | Content of limulus test-positive glycolipid (ng) |
|---|---|
| Gymnosperm | |
| Pinus spp. (Konan Boeki Co. in Japan) | 125 |
| Monocotyledoneae | |
| Hard wheat seeds (Chiba Flour Milling Co. Ltd. in Japan) | 2,250 |
| Hard wheat seeds (m.w.: 5,000 or more) (Chiba Flour Milling Co. Ltd.) | 1,0000,000 |
| Hard wheat flour (Chiba Flour Milling Co. Ltd.) | 7,500 |
| Wheat bran (m.w.: 5000 or more) (Chiba Flour Milling Co. Ltd.) | 300 |
| Wheat germ (Chiba Flour Milling Co. Ltd.) | 1,600 |
| Wheat germ (m.w.: 5000 or more) (Chiba Flour Milling Co. Ltd.) | <10,000 |
| Unpolished rice | 1,100 |
| Rice flour (m.w.: 5000 or more) (Hinomoto Koku-fun Co. in Japan) | 31,000,000 |
| Rice bran | 29,000 |
| Rice bran (m.w.: 5000 or more) | 500,000 |
| Corn flour (m.w.: 5000 or more) (Taiyo Shiro Co. in Japan) | <0.3 |
| Corn grits (m.w.: 5000 or more) (Taiyo Shiro Co. in Japan) | 120 |
| Corn (Wako Shokuryo Co. in Japan) | 200 |
| Gramineae Sasa (Sekimoto Bussan Co. in Japan) | 15,000 |
| Iridaceae Iris (seeds) | 3,300 |
| Garlic (bulb) | 70 |
| Asparagus (bud) | 4,500 |
| Zingiber mioga (flower) | 41,000 |
| Coix Lacryma-jobi L. var. Ma-yuen Stapf (Uchida Wakan-yaku Co. in Japan) | 2,300 |
| Pinellia ternata (Thunb) Breitenbach (Matsu-ura Yakugyo Co. in Japan) | 5,500 |
| Ophiopogon japonicus Ker-Gawl. var. genuinus Maxim., O. japonicus Ker-Gawl. (Tochigi Tenkaido Co. in Japan) | 4,000 |
| Turmeric (SB Shokuhin Co. in Japan) | 195,000 |
| Dicotyledoneae | |
| Soybean (Sanyo Shokuhin Co. in Japan) | 150 |
| Soybean (m.w.: 5,000 or more) (Hokuren Co. in Japan) | 400 |
| "Adzuki" bean (Wako Shokuryo Co. in Japan) | 450 |
| "Adzuki" bean (m.w.: 5,000 or more) (Wako Shokuryo Co.) | 36,000,000 |
| Broad bean (raw) | 750 |
| Potato (m.w.: 5,000 or more) (Hokuren Co.) | <0.3 |
| Japanese medlar (seed) | 800 |
| Avocado (seed) | 950 |
| Peach (seed) | 4,500 |
| Walnut (seed) | 1,900 |
| Broad bean (seed) | 750 |
| Pumpkin (seed) | 10,000 |
| Tomato (raw berry) | 10,500 |
| "Kaiware daikon" (Japanese radish) (except root) | 50,000 |
| Actinidia polygama Maxim. (Marukyu Bussan Co. in Japan) | 40,000 |
| Gynostemma pentaphyllum (Thunb.) Makino (K.K. Sakurai in Japan) | 73,000 |
| Houttuynia cardata Thunb (on wet weight | 1,200 |

TABLE 2-continued

| | |
|---|---|
| basis) | |
| (Medicinal plant garden belonging to Teikyo University in Japan) | |
| White pepper (SB Shokuhin Co.) | 2,300 |
| Capsicum annuum L. (Konan Boeki Co. in Japan) | 2,300 |
| Illicium verum Hook. fil. (Konan Boeki Co.) | 5,500 |
| Nutmeg (Lion Co. in Japan) | 2,000 |
| Sour orange (Uchida Wakanyaku Co.) | 8,000 |
| Kudzu-vine (Tochigi Tenkaido Co.) | 3,000 |
| Glycyrrhiza glabra L. var. glandulifera Regal et Herder (Uchida Wakanyaku Co.) | 18,000 |
| Carrot (Uchida Wakanyaku Co.) | 45,000 |
| Seseli libanotis Koch var. daucifolia DC. (Tochigi Tenkaido Co.) | 50,000 |
| Sinomenium acutum Rehd. et Wils (Tochigi Tenkaido Co.) | 600,000 |
| Uncaria rhynchophylla Miq., Ourouparia rhynchophylla Matsum. (Uchida Wakanyaku Co.) | 7,000 |
| Pteridophyta | |
| Horse tail (on wet weight basis) (Medicinal plant garden belonging to Teikyo University in Japan) | 700 |
| Royal fern (Sekimoto Bussan Co. in Japan) | 10,000 |
| Algae | |
| Undaria pinnatifida Suringar (Sanriku district in Japan) | 11,000 |
| Bud of Undaria pinnatifida Suringar | 200,000 |
| Hijikia fusiformis (raw) | 85,000 |
| Bud of Hijikia fusiformis (Sho-zen Hon-ten in Japan) | 105,000 |
| Kelb (Yamato Takahasi Co. in Japan) | 235,000 |
| Asakusa laver (dried raw laver) | 130,000 |
| Chlorella | |
| (Healstar Japan YS Co. in Japan) | 1,900,000 |
| (Mannan foods YS Co. in Japan) | 1,000,000 |
| Fungi | |
| Lentinus edodes Sing., Cortinellus shiitake P. Henn. (Shimonita in Shizuoka, Japan) | 16,000 |
| Winter mushroom (Nakano City in Nagano, Japan) | 20,000 |
| Lyophyllum shimeji (Seta-gun, Miyagi-machi in Gunma, Japan) | 40,000 |
| Polyporales Grifola (Ohtone in Japan) | 205,000 |
| Mushroom | 20,000 |
| Jew's ear | 75,000 |
| Pholiota nameko | 21,000 |
| Brewers yeast | 250,000 |
| Cordyceps sinensis Sacc., Cordyceps sobolifera | 240,000 |

| Sample (Liquid) | Limulus test-positive glucolipid (ng) |
|---|---|
| Beer | |
| Kirin's | |
| FINE PILSNER | 1,150 |
| LAGER BEER | 1,250 |
| HEARTLAND | 1,550 |
| FINE DRAFT | 1,400 |
| Asahi's SUPER YEAST | 600 |
| Wine | |
| Suntory's Ste. Neige | |
| (white) | 13 |
| (red) | 24 |
| Cidre (apple) | 900 |
| Sake (Japanese liquor) | |
| Ozeki, first grade (Ozeki Shuzo Co.) | 2.4 |
| Kizakura, second grade (Kizakura Shuzo Co.) | 1.7 |
| Taikan Ginio, second grade (Gyokusendo Shuzo Co.) | 2.1 |
| Sake from unpolished rice | |
| Hibi Ikkon (Ozeki Shuzo Co.) | 12 |
| Herb liquor | |
| Totoshu DELCUP (Totoshu Honpo Co. in Japan) | 1.2 |
| Shochu (Japanese low-class distilled spirits) | |
| TAKARA SHOCHU (Takara Shuzo Co. in Japan) | <2.0 |
| Others | |
| KYOLEOPIN (Wakunaga Seiyaku Co. in Japan) | 600 |
| Garlic extracts (Wakunaga Seiyaku Co.) | 350 |

Experiment 2

A. Determination of Endogenous TNF Production Stimulation

1) Zero point two ml of physiological saline containing the respective test samples dissolved therein as primers was injected into 7 week old C3H/He female mice via caudal vein; each group consisted of three mice having an average weight of 25 g Three hours later 1 KE of OK-432 as a trigger was administered to the animals via caudal vein. Here "ME" is a Klinische Einheit unit, and 1 ME corresponds to the quantity of a preparation containing 0.1 mg of dried cells. Two hours later the serum was collected to determine its TNF activity on the basis of the toxicity to L929 cells. The results calculated as an average of three per group are shown in FIG. 4.

Figure 4:
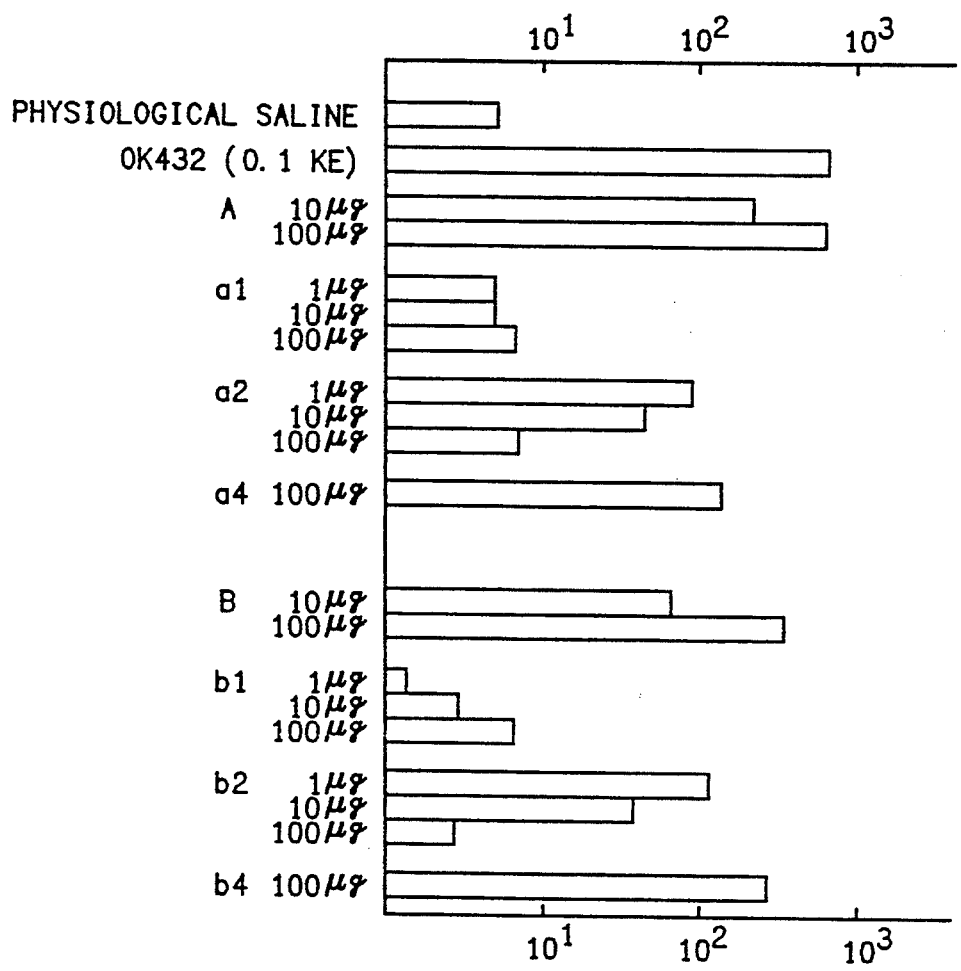
FIG. 4 is a graph demonstrating the endogenous TNF production stimulation of the limulus test-positive plant glycolipid of the present invention when it is administered intravenously, in comparison with that of a control or one of the prior art immuno stimulators.
Figure 8A:
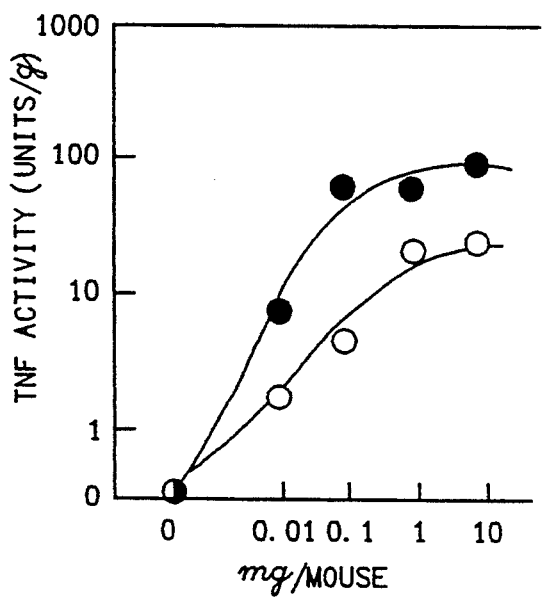
FIGS. 8a, 8b, 8c, and 8d are graphs showing the endogenous TNF productivity of the limulus test-positive plant glycolipid of the present invention.
Figure 8B:
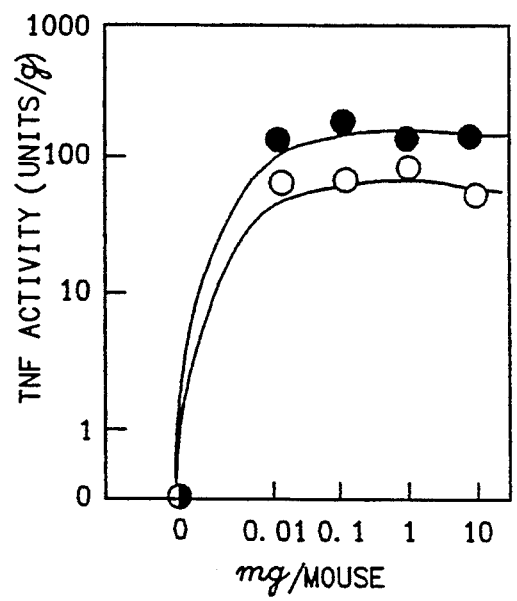
Figure 8C:
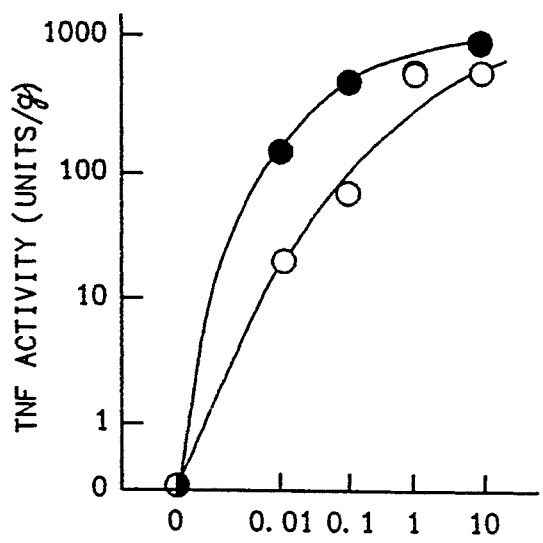
Figure 8D:
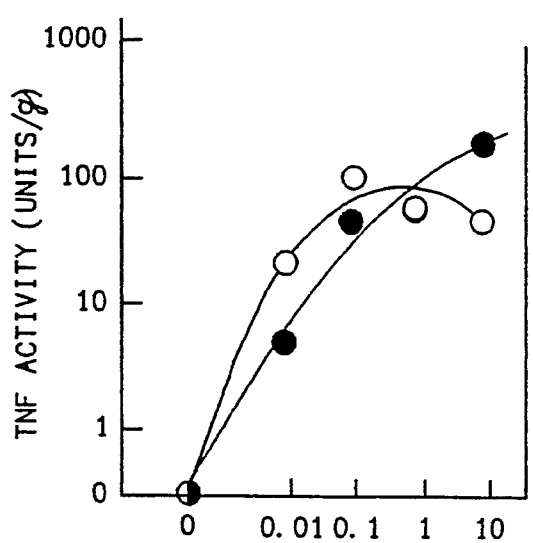

It is apparent from FIG. 4 that the limulus test-positive plant glycolipid of the present invention has the same degree of endogenous TNF production stimulation as OK-432. Further, it is supposed that the limulus test-positive plant glycolipid of the present invention effects the maximum stimulation of endogenous TNF production at a certain quantity.

2) Separately, the respective test samples as primers were administered orally to the respective groups consisting of three mice (7 week old female C3H/He, average weight: 25 g). Here, each of the test samples was dissolved in 200 μl of distilled water, and then administered directly into the stomach with an oral sonde, and then treated in the same manner as in the above case of intravenous administration. The results calculated as an average of three per group are shown in FIG. 5.

FIG. 5 apparently shows that the limulus test-positive plant glycolipid of the present invention stimulates the production of endogenous TNF even when it is administered orally.

3) Zero point two ml of physiological saline containing various proportions of Powder A-$a_2$ obtained in Example 1 as a primer was injected into 12 week old C3H/He male mice via caudal vein; each group consisted of three mice having an average weight of 29 g. Three hours later 0.2 ml of physiological saline dissolving 1.0 or 3.0 KE of OK-432 therein as a trigger was administered to the animals via caudal vein. Two hours later the serum was collected to determine its TNF activity on the basis of the toxicity to L929 cells. The results calculated as an average of three per group are shown in FIG. 6.

It is apparent from FIG. 6 that the limulus test-positive plant glycolipid of the present invention effects the maximum stimulation of endogenous TNF production at a certain quantity.

4) Separately, 0.2 ml of physiological saline containing Powder A-$a_2$ obtained in Example 1 as a primer (in terms of E. coli LPS, 1 μg of the limulus test-positive plant glycolipid of the present invention was contained) was injected into 9 week old C3H/He male mice via caudal vein. Here, each group consisted of three mice having an average weight of 27 g, and the Powder A-$a_2$. Three hours later 0.2 ml of physiological saline dissolving 1.0 or 3.0 KE of OK-432 therein as a trigger was administered to the animals via caudal vein. Two hours later the serum was collected to determine its TNF activity on the basis of the toxicity to L929 cells. The results calculated as an average of three per group are shown in FIG. 7 where the axis of abscissa shows the administration interval of the primer and the trigger.

It is apparent from FIG. 7 that the administration interval of the primer and the trigger should be considered in order to accomplish the maximum stimulation of the endogenous TNF production.

B. Determination of Endogenous TNF Productivity

1) Zero point two ml of physiological saline containing Powder A-a$_2$ obtained in Example 1 as a primer ( in terms of E. coli LPS, 1 μg of the limulus test-positive plant glycolipid of the present invention was contained) or only physiological saline (control group) was injected into 9 week old C3H/He male mice via caudal vein; each group consisted of three mice having an average weight of 27 g. Three hours later 0.2 ml of physiological saline dissolving 0–10 mg of Powder A-a$_2$ as a trigger was administered to the animals via caudal vein. One hour after the administration of the trigger, the serum, liver, spleen and lung were isolated to determine the TNF activity on the basis of the toxicity to L929 cells. Results calculated as an average of three animals per group are shown in FIGS. 8a, 8b, 8c, and 8d, where 8a represents data for the serum, 8b for the liver, 8c for the spleen, and 8d for the lung, respectively.

It is apparent from FIGS. 8a, 8b, 8c, and 8d that the limulus test-positive plant glycolipid of the present invention is also useful as a trigger.

2) Separately, 0.2 ml of physiological saline containing 1,000 units of any one of the various TNFs shown in Table 3 given below as a primer or only physiological saline (control group) was injected into 9 week old C3H/He male mice via caudal vein; each group consisted of three mice having an average weight of 29 g. Three hours later 0.2 ml of physiological saline dissolving therein 1 mg of Powder A-a$_2$ of the present invention obtained in Example 1 was administered to the animals via caudal vein as a trigger. One hour after the administration of the trigger, the serum was collected to determine the TNF activity on the basis of the toxicity to L929 cells. The results calculated as an average of three per group are shown in FIG. 9.

TABLE 3

| Primers used | |
| --- | --- |
| r-TNF-S-AM2 | (disclosed in Example 1 of Japanese patent application disclosure No. HEI 1-95784) |
| mouse TNF-α | (Proci. Natl. Acad. Sci. U.S.A., 82, pp. 6060–6064, 1985) |
| Thymosin β$_4$/TNF-S$_{AM1}$ | (Biochemisrty International, vol. 18,. No. 3, pp. 501–508, 1989) |

Figure 9:
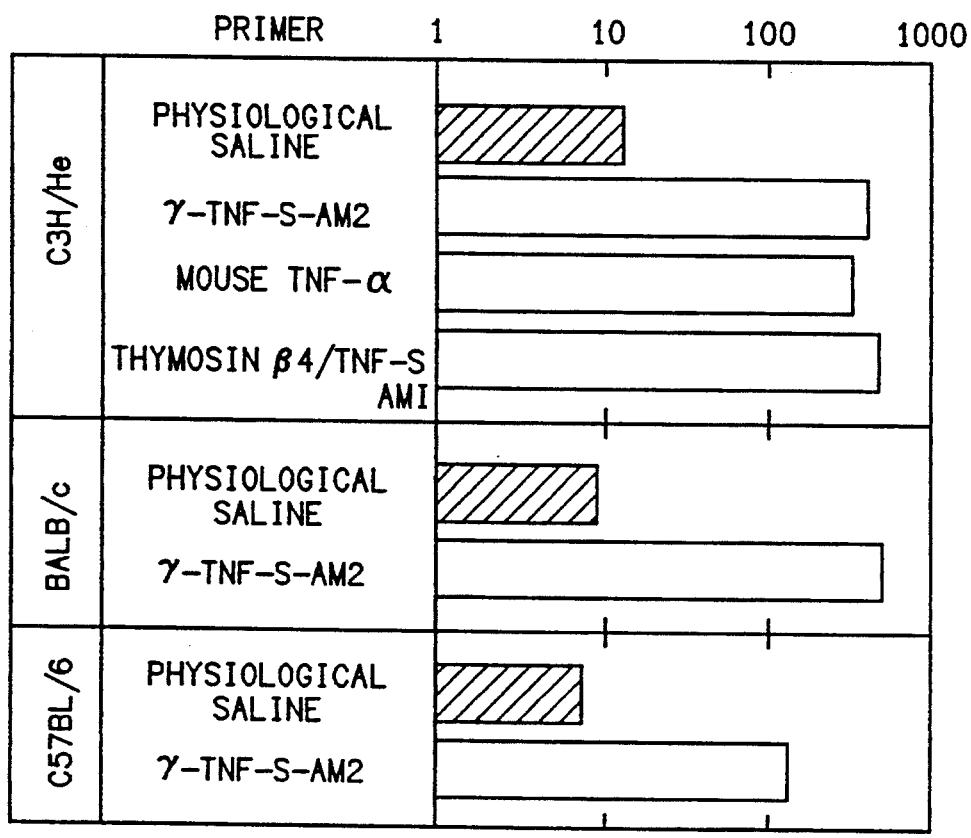
FIG. 9 is a graph showing that the endogenous TNF productivity of the limulus test-positive plant glycolipid of the present invention drastically increases in case a variety of TNFs are used as endogenous TNF production stimulators.

FIG. 9 clearly shows that the endogenous TNF productivity of the limulus test-positive plant glycolipid of the present invention increases to about thirty times as much as the original when a TNF is used as a primer.

Figure 10:
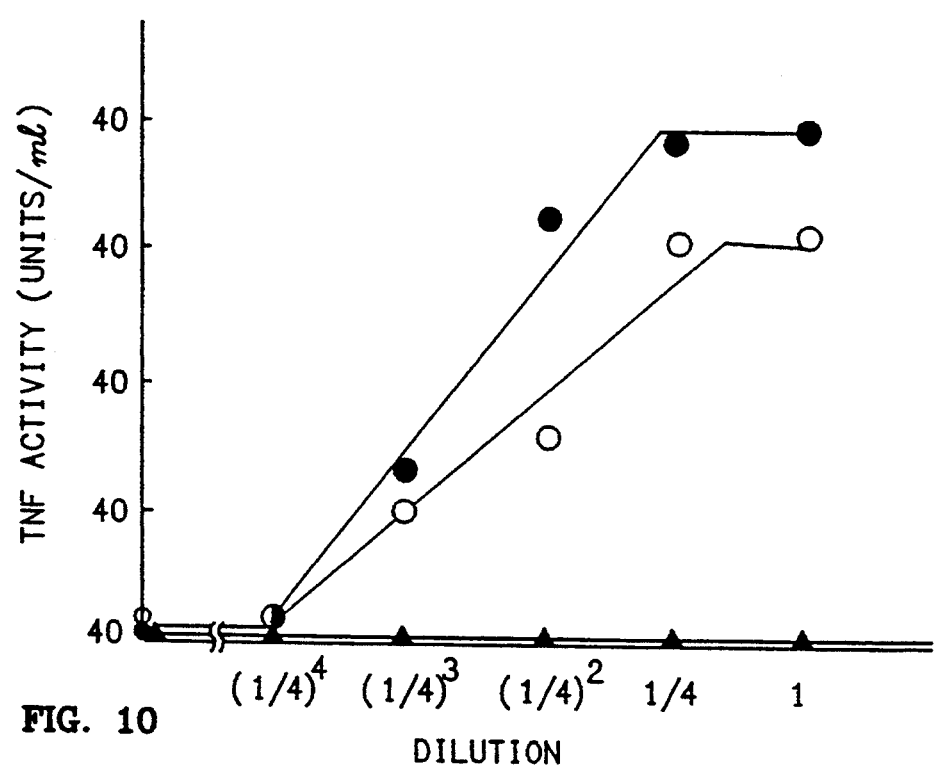
FIG. 10 is a graph showing the endogenous TNF productivity of the limulus test-positive plant glycolipid of the present invention in comparison with that of *E. coli* LPS.

3) Separately, 200 μl (2×10$^5$ cells)/well of macrophage peritoneal cells of mice were placed in a flat-bottomed having 96 wells, and 10 μl of recombinant IFN-γ (100 units/ml) as a primer was placed in the respective wells. Three hours later, as the trigger, 10 μl/well of Powder A-a$_2$ of the present invention described in Example 1 (2 mg/ml) or E. coli LPS (1 μg/ml) was added followed by culturing for 2 hours. A pipette was used to collect 130 μl of the supernatant from the respective wells, and the TNF activity was determined on the basis of the toxicity to L929 cells. The results calculated as an average of three per group are shown in FIG. 10. In FIG. 10, ○ shows the data of Powder A-a$_2$ of Example 1 which is a member of the limulus test-positive plant glycolipid of the present invention, ● shows the data of E. coli LPS. Further, ▲ shows the direct toxicity of Power A-a$_2$ and E. coli LPS to L929 cells; the values were zero in the two cases.

It is evident from FIG. 10 that the endogenous TNF productivity of the limulus test-positive plant glycolipid of the present invention is on the same level as that of E. coli LPS.

Figure 11:
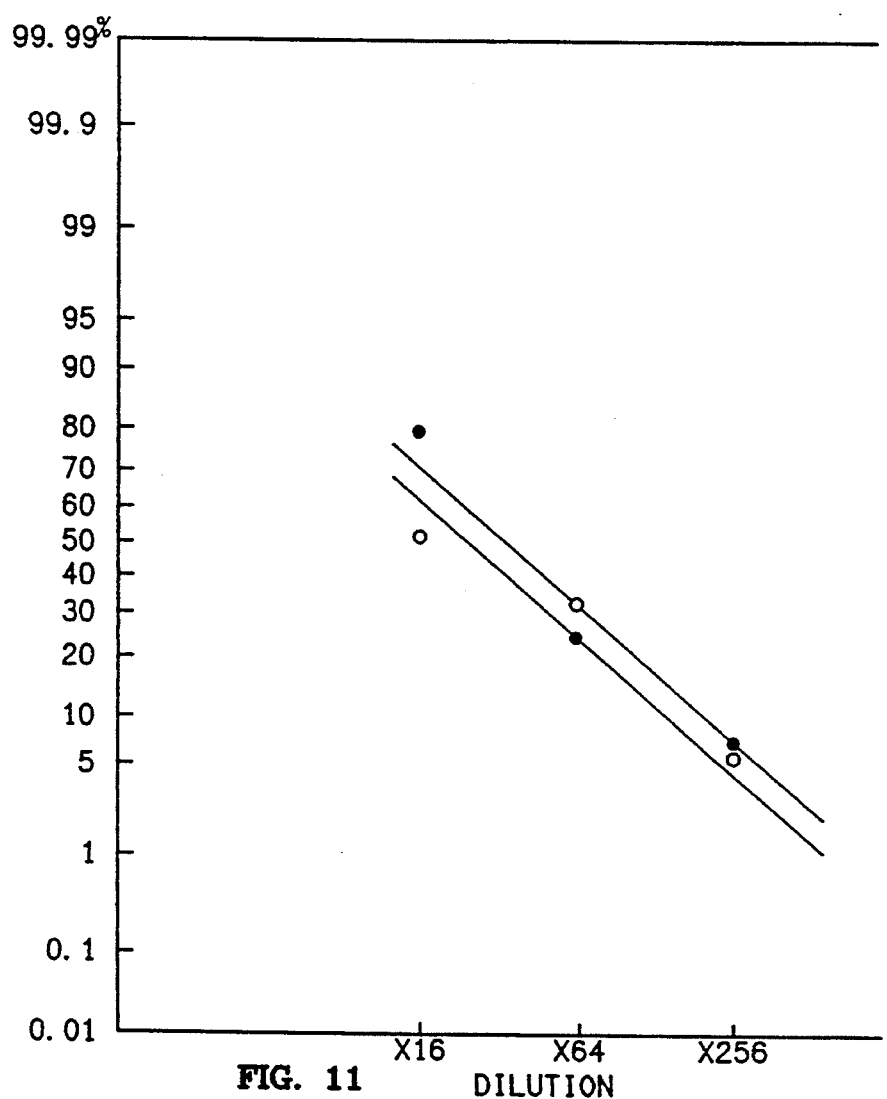
FIG. 11 is a logarithmic normal probability sheet showing the endogenous TNF productivity of the limulus test-positive plant glycolipid of the present invention in comparison with the content of said glycolipid determined according to the limulus test.

FIG. 11 shows a probability analysis of the endogenous TNF productivity of the limulus test-positive plant glycolipid of the present invention shown in FIG. 10 and the content of the limulus test-positive plant glycolipid of the present invention determined according to the limulus test.

FIG. 11 proves that the content of the limulus test-positive plant glycolipid of the present invention is highly correlated with the endogenous TNF productivity, and thus, no doubt the limulus test-positive plant glycolipid of the present invention has endogenous TNF productivity.

c. Influence of Difference on Endogenous TNF Produciton Stimulation and TNF Productivity 1) Zero point two ml of physiological saline containing 1 or 3 μg (in terms of limulus activity) of CHF was injected into 7 week old C3H/He male mice via caudal vein; each group consisted of two mice having an average weight of 25 g. One hour later the serum was collected to determine the TNF activity on the basis of the toxicity to L929 cells. The results calculated as an average of two per group are shown in Table 4 given below.

TABLE 4

| Trigger | TNF activity (units/ml) |
| --- | --- |
| Physiological saline (control) | 0 |
| Powder A-a$_2$ 1 μg | 9.6 ± 2.0 |
| CHF (number of P: 1 /mol) 1 μg | 13.0 ± 0.1 |
| CHF (number of P: 1 /mol) 3 μg | 59.0 ± 0.0 |

2) Zero point two ml of physiological saline containing, as the primer, 1 ng (in terms of limulus activity) of CHF which was assumed to have three phosphoruses per molecule or only physiological saline was injected into 7 week old BALB/c male mice via caudal vein; each group consisted of two mice having an average weight of 25 g. Three hours later, 0.2 ml of physiological saline containing 1 KE of Ok-432 dissolved therein was injected also via caudal vein. Two hours later the serum was collected to determine the TNF activity on the basis of the toxicity to L929 cells. The results calculated as an average of two per group are shown in Table 5 given below.

TABLE 5

| Dose of CHF (number of P: 3/mol) as primer (ng) | TNF activity (units/ml) |
| --- | --- |
| 0 | 4.7 ± 1.4 |

TABLE 5-continued

| Dose of CHF (number of P: 3/mol) as primer (ng) | TNF activity (units/ml) |
| --- | --- |
| 1 | 560 ± 180 |

3) Zero point two ml of physiological saline containing, as the primer, 1 ng (in terms of limulus activity) of CHF which was assumed to have three phosphoruses per molecule or 1 ng of E. coli LPS was injected into 7 week old BALB/c male mice via caudal vein; each group consisted of two mice having an average weight of 25 g. Three hours later, 0.2 ml of physiological saline containing 1 μg (in terms of limulus activity) of CHF or 1 μg of E. coli LPS dissolved therein as the trigger was injected also via caudal vein. One hour later after the injection of the trigger the serum was collected to determine the TNF activity on the basis of the toxicity to L929 cells. The results calculated as an average of two per group are shown in Table 6 given below.

TABLE 6

| Sample | TNF activity (units/ml) |
| --- | --- |
| CHF - CHF | 20 ± 17 |
| E. coli LPS - E. coli LPS | 20 ± 13 |

Judging from the results shown in Tables 4 and 6, it is supposed that the presence of at least one phoshorus in the is enough to prevent lowering of the TNF production stimulation and productivity.

Experiment 3: Determination of Stimulation of Localized Production of TNF

Powder A-a₂ was suspended in physiological saline to prepare 0.2 ml of suspension containing 20 μg of the limulus test-positive plant glycolipid of the present invention was injected into 7 week old BALB/c male mice bearing fibra Meth A via caudal vein; each group consisted of three mice having an average weight of 24 g. Then the change in the quantity of the TNF in the serum, tumor tissue, liver, lung and spleen with time was observed over six hours. The determination was effected using asn indication the toxicity to L929 cells. The results calculated as an average of three per group are shown in FIG. 12 In FIG. 12, ●, ▲, ▽, □ and ■ show the data of the serum, tumor tissue, liver, ling and spleen, respectively.

Figure 12:
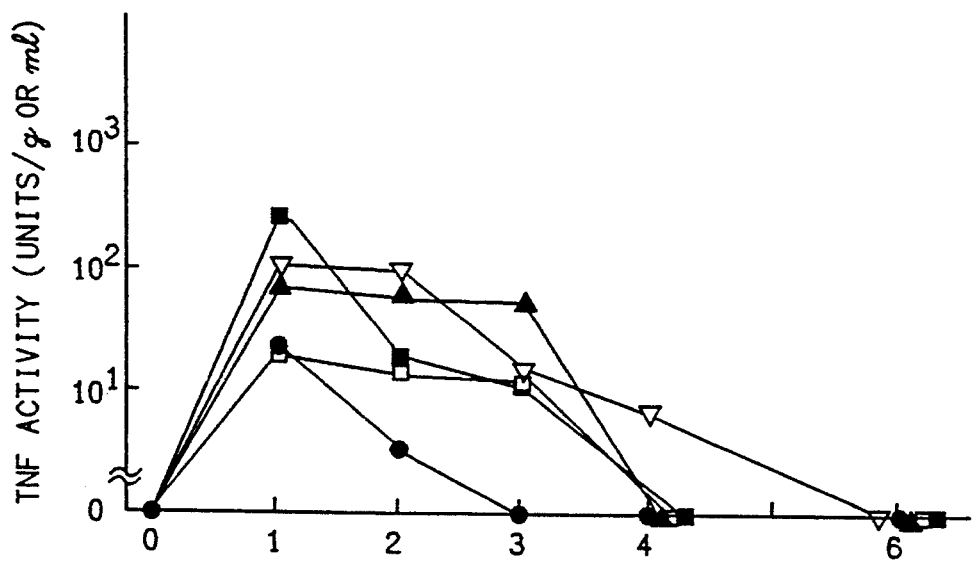
FIG. 12 shows the stimulation of localized production of TNF by the limulus test-positive plant glycolipid of the present invention.

FIG. 12 demonstrates that the production of TNF in tremor tissue last for a long time.

Experiment 4: Determination of Immuno Stimulation by Subcutaneous Administration A. Stimulation of endogenous TNF production 1) 200 ml of physiological saline (Group A) or 200 ml of physiological saline containing 1 μg of Powder A-a₂ obtained in Example 1 suspended therein (Group B) as primers was injected into 6 week old BALB/c nu/nu male mice via caudal vein; each group consisted of two mice having a weight range of 19–23 g, or 50% aqueous glycerin containing 1 mg/ml of Powder A-a₂ obtained in Example 1 was applied all over the abdomen three or six times at intervals of 20 minutes ( 100 μl at one application) (Group C).

2) Three hours after the intravenous injection or application was comleted, 1 KE of OK-432 as a trigger was administered to the animals via caudal vein. Two hours later the serum was collected to determine the TNF activity of their 20 μl fractions on the basis of the toxicity to L929 cells. The results calculated as an average of two per group are shown in Table 7.

TABLE 7

| Group A | 2 units/ml |
| --- | --- |
| Group B | 270 units/ml |
| Group C | 8 units/ml |

B. Carbon Removal Activity

1) A 50% aqueous glycerin solution (Group A), a 50% aqueous glycerin solution containing 1 mg/ml of Powder A-a₂ obtained in Example 1 (Group B) or a 50% aqueous glycerin solution containing 2 μg/ml of E. coli LPS was applied to the abdomen of 10 week old BALB/c male mouse once a day for 5 days; the respective groups consisted of three mice having an average weight of 24–29 g, and 50 μl was applied each time. Five days later 200 μl of physiological saline containing 15 μg/ml of E. coli LPS was injected to mice of Group D via caudal vein.

2) Two days after the last application in Groups A to C or the intravenous injection in Group D, a carbon. Rotring Ink Art 591017 ( manufactured by Rotring Ink Co. in W. Germany) was prepared as a 6-fold dilution with physiological saline, and injected to the respective mice in a proportion of one hundredth of the respective body weights via caudal vein.

3) The blood was collected 5 minutes after the end of the intravenous injection of the carbon, and the respective whole blood (20 μl) was diluted with 2 ml of 1% $Na_2CO_3$, and the carbon content was measured optically as $OD_{660}$. The results calculated as an average of three per group are shown in Table 8 given below.

In the table, Group E is the group of mice from which blood was collected immediately after the intravenous injection of the carbon, and thus the carbon removal activity in this case is estimated to be "0". Group F is the group of mice not treated, and the optical data of the 20 μl portions of their blood is utilized as background.

The carbon removal rates were calculated according to the following equation:

$$\left(1 - \frac{(\text{value of each group}) - (\text{value of Group F})}{(\text{value of Group E}) - (\text{value of Group F})}\right) \times 100$$

TABLE 8

| Group | $OD_{660}$ | Carbon removal (%) |
| --- | --- | --- |
| A | 0.547 | 24 |
| B | 0.450 | 53 |
| C | 0.480 | 44 |
| D | 0.320 | 93 |
| E | 0.625 | 0 |
| F | 0.296 | — |

Experiment 5: Determination of Osteogenesis Stimulation

1) The left and right parietal bones (totally 2 parietal bones exist) of fowl's embryo 18 days after it hatched were taken out, and placed in separate test tubes containing 1 ml of complete synthetic medium BGJb-HW2 (the composition is shown below) comprising $^{45}Ca$ (0.5 μCi/ml as $^{45}CaCl$), and then incubated for 2 hours in a water bath to label the bones with $^{45}Ca$.

| Components | Content (mg/l) |
|---|---|
| L-Lysine HCl | 240 |
| L-histidine HCl.H2O | 150 |
| L-arginine HCl | 75 |
| L-threonine | 75 |
| L-valine | 65 |
| L-leucine | 50 |
| L-isoleucine | 30 |
| L-methionine | 50 |
| L-phenylalanine | 50 |
| L-tryptophan | 40 |
| L-tyrosine | 40 |
| L-cysteine HCl-H2O | 90 |
| L-glutamine | 200 |
| glycine | 150 |
| L-serine | 105 |
| L-proline | 115 |
| nicotinamide | 20 |
| thiamine HCl | 4 |
| potassium pantothenate | 0.2 |
| riboflavin | 0.2 |
| pyridoxal phosphate | 0.2 |
| folic acid | 0.2 |
| biotin | 0.2 |
| p-aminobenzoic acid | 2 |
| α-tocopherol phosphate Na | 1 |
| choline chloride | 50 |
| m-inositol | 0.2 |
| cyanocobalamin | 0.04 |
| NaCl, dried | 8,000 |
| KCl, dried | 400 |
| $CaCl_2$, anhydrous | 139.7 |
| $MgSO_4$, anhydrous | 97.7 |
| $Na_2HPO_4.2H_2O$ | 60.1 |
| Dried sample of the above | 47.9 |
| $KH_2PO_4$ | 160 |
| $FeCl_3.6H_2O$ | 0.47 |
| glucose, dried | 5,000 |
| (the foregoing components are dissolved in distilled water to prepare a 1 l solution to which the following components are added.) | |
| calf serum albumin | 10 |
| $NaHCO_3$ | 1,400 |
| L-ascorbic acid Na | 50 |
| penicillin G - K salt | 10 |
| streptomycin | 10 |
| Phenol Red | appropriate |

2) After this labelling, the respective parietal bones were washed with PBS (-) (Nissui Co.) and then placed in separate incubation tubes each containing 1 ml of non-labelled complete synthetic medium BGJb-HW2 and the tubes were capped. Incubation was effected overnight at 30° C. using a rotary incubator. The leaking of the $^{45}Ca$ into the medium during this incubation term was judged to be due to physico-chemical exchange reactions, but not due to bony tissue absorbing activity, and the medium was discarded.

3) One of the two parietal bones was placed in an incubation tube containing only 1 ml of non-labelled complete synthetic medium BGJb-HW2, and the other was placed in a separate incubation tube containing not only only 1 ml of non-labelled complete synthetic medium BGJb-HW2 but Powder A-$a_2$ obtained in Example 1 which is the limulus test-positive plant glycolipid of the present invention, and the two tubes capped and incubated in a rotary incubator overnight.

4) The medium (each, 250 μl) was added to 4.5 ml of ACSII scintillator (Amersham Co. In U.K.), and the counting was made on the basis of liquid scintillation to determine the quantity of the 45Ca leaked into the medium.

5) After the incubation, the respective parietal bones were washed with PBS (-), and then moved to other incubation tubes each containing 1 ml of 1N HCl, and the tubes were capped and then allowed to stand at room temperature over night. The medium (each, 250 μl) was added to 4.5 ml of ACSII scintillator, and the counting was made on the basis of liquid scintillation to determine the quantity of the 45Ca remaining in the bones. The results calculated as an average of five samples are shown in Table 9 given below.

TABLE 9

| Sample | $^{45}Ca$ leakage | | T/C rate |
|---|---|---|---|
| | Control C | Treated T | |
| PTH (/ml) | | | |
| 1 unit | 3.67 | 4.46 | 1.22 |
| Powder A (/ml) | | | |
| 10 μg | 3.84 | 5.15 | 1.34 |
| 1 μg | 4.47 | 5.05 | 1.13 |
| 0.1 μg | 3.99 | 4.05 | 1.02 |
| 0.01 μg | 3.98 | 3.97 | 1.00 |

PTH = Already known parathyroid hormone which is a bony tissue absorbance hormone. Its one unit corresponds to about 1 μg.

As is apparent from the data shown in the above table, the effect of Power A increases as the dose increase, and the use of 10 μg is more effective than the use of about 1 μg of PTH. The supply of PTH is very small, and it is very expensive. So, Powder A, one member of the limulus test-positive plant glycolipid of the present invention may be used as a very cheap and much supplied substitute for PTH.

Experiment 6: Determination of Stimulation of Oviposition and Shell Strength Improvement Powder A obtained in Example 1 was dissolved in water and the resulting solution was given to domestic fowls at a rate of about 350 ml per day for 16 days. The count of the eggs and their shell strength of the respective fowls were investigated every day for 30 days including the day on which the solution was given.

The fowls were divided into three groups depending on the quantity of Powder A given. Each group consisted of 6 fowls.

Group X: 600 mg/ml
Group Y: 60 mg/ml
Group Z: Water (control)

The results are shown in Table 10 given below.

TABLE 10

| | | Group X | Group Y | Group Z |
|---|---|---|---|---|
| Total of eggs (total of six fowls in each group) | during dosing | 80 | 66 | 63 |
| | after dosing | 85 | 67 | 66 |
| | total S | 165 | 133 | 129 |
| Count of eggs having shell strength of 4 kg/cm² or more (total of six fowls in each group) | during dosing | 29 | 17 | 9 |
| | after dosing | 24 | 17 | 7 |
| | total T | 53 | 34 | 16 |
| T/S × 100(%) | | 32 | 26 | 12 |

The following three points have been made apparent by the data given in the above Table 10.

1) The counts of eggs in Groups X and Y to which Power A, one member of the limulus test-positive plant glycolipid of the present invention, was given are larger than that of Group Z. Particularly, the count of Group X is 1.5 times (165 divided by 129) as many as that of Group Z. Accordingly, the limulus test-positive plant glycolipid of the present invention is judged to have oviposition stimulation.

2) The rates of the counts of eggs having a shell strength of 4 kg/cm² or more to the toal counts of eggs in Groups X and Y to which Power A, one member of the limulus test-positive plant glycolipid of the present invention, was given is twice or more than that of Group Z. Accordingly, the limulus test-positive plant glycolipid of the present invention is judged to have excellent oviposition stimulation.

3) The stimulation of oviposition and shell strength improvement was observed even after the dosing was stopped. So, the activity of the limulus test-positive plant glycolipid of the present invention is judged to last for a long time.

Dose, Interval and Toxicity

Judging of the nature of immuno stimulators, the dose and the interval of the limulus test-positive plant glycolipid of the present invention when it is used as an immuno stimulator or a veterinary immuno stimulator are of course determined by the doctor or veterinarian in charge individually in view of the age, conditions, etc of the patient and the quantity of TNF expected to be produced. However, it may be said that 0.1 to 200 µg (in the case of 100% purity) is a standard dose to adults (body weight 50 kg).

95% purity sample of the limulus test-positive plant glycolipid of the present invention was administered to three to six weeks old BALB/c male mice (body weight: 19–23 g) intravenously, and the mice were observed for 48 hours. As a result, no death was confirmed. No acute toxicity was abserved for adults (50 kg) to which 15 g (in terms of active ingredient) of the glycolipid of the present invention were given. Here, the LD$_{50}$ of *E. coli* LPS to the same type mice as mentioned above was 8.4 mg/kg, so the safety of the the limulus test-positive plant glycolipid of the present invention is very reliable.

What we claim is:

1. A method of stimulating the immune system of an animal in need of such immune system stimulation, comprising administering to said animal an effective amount of a limulus test-positive plant glycolipid wherein the limulus test-positive plant glycolipid has the following properties:

Molecular weight: 8,000 ±1,000 (SDS electrophoresis)
   Number of phosphorus: not less than 1 per mol
   Number of hexosamine: 6 ±2 per mol
   Number of fatty acid moieties: 6 ±2 per mol.

2. The method according to claim 1, wherein the animal is a mammal and the immune system stimulation is osteogenesis.

3. The method according to claim 1, wherein the animal is an egg-bearing non-mammalian animal and the immune system stimulation is selected from the group consisting of oviposition and egg shell strength improvement.

4. The method according to claim 1, wherein the limulus test-positive plant glycolipid is obtained from a plant selected from the group consisting of Gymnospermae, Monocotyledoneae, Dicotyledoneae, Pteridophyta and Algae.

5. The method according to claim 4, wherein the Monocotyledoneae plant is Gramineae.

6. The method according to claim 5, wherein the Gramineae plant is rice.

7. The method according to claim 5, wherein the Gramineae plant is selected from the group consisting of wheat, barley, rye, and oat.

8. The method according to claim 4, wherein the Algae plant is selected from the group consisting of Phaenophyceae, Rhodophyceae, Chlorophyceae and Cyanophyceae.

9. The method according to claim 8, wherein the Chlorophyceae plant is chlorella.

10. The method according to claim 1, wherein the limulus test-positive plant glycolipid is obtained from a fungus.

11. The method according to claim 10, wherein the fungus is Basidiomycetes or Ascomycetes.

* * * * *